United States Patent
Schneider et al.

(10) Patent No.: US 8,781,180 B2
(45) Date of Patent: *Jul. 15, 2014

(54) BIOMETRIC SCANNER WITH WAVEGUIDE ARRAY

(75) Inventors: John K. Schneider, Snyder, NY (US); Jack C. Kitchens, Tonawanda, NY (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/423,523

(22) Filed: Mar. 19, 2012

(65) Prior Publication Data

US 2012/0206585 A1 Aug. 16, 2012

Related U.S. Application Data

(63) Continuation of application No. 11/754,131, filed on May 25, 2007, now Pat. No. 8,139,827.

(60) Provisional application No. 60/803,150, filed on May 25, 2006, provisional application No. 60/822,087, filed on Aug. 11, 2006.

(51) Int. Cl.
*G06K 9/00* (2006.01)

(52) U.S. Cl.
USPC .......................................................... 382/123

(58) Field of Classification Search
None
See application file for complete search history.

(56) References Cited

U.S. PATENT DOCUMENTS

| | | |
|---|---|---|
| 3,736,436 A | 5/1973 | Crites |
| 3,736,552 A | 5/1973 | Sessler et al. |
| 3,778,756 A | 12/1973 | Houston et al. |
| 3,786,495 A | 1/1974 | Spence |
| 4,211,949 A | 7/1980 | Brisken et al. |
| 4,245,329 A | 1/1981 | Dubois |
| 4,385,831 A | 5/1983 | Ruell |
| 4,434,799 A | 3/1984 | Taenzer |
| 4,730,495 A | 3/1988 | Green |
| 4,910,840 A | 3/1990 | Sprenkels et al. |
| 5,061,071 A | 10/1991 | Fujita et al. |
| 5,768,010 A | 6/1998 | Iwamoto |
| 6,445,109 B2 | 9/2002 | Percin et al. |
| 6,552,841 B1 | 4/2003 | Lasser et al. |
| 6,702,747 B2 | 3/2004 | Garlick |
| 6,926,672 B2 | 8/2005 | Moore et al. |
| 6,974,417 B2 | 12/2005 | Lockwood et al. |

(Continued)

FOREIGN PATENT DOCUMENTS

WO 2006042144 A2 4/2006

OTHER PUBLICATIONS

International Search Report and Written Opinion—PCT/US2007/069791—ISA/EPO—Sep. 16, 2008.

*Primary Examiner* — Chan S Park
*Assistant Examiner* — Elisa Rice
(74) *Attorney, Agent, or Firm* — Hodgson Russ LLP

(57) ABSTRACT

Devices and methods of creating an image of a biological object are disclosed. In one embodiment of the invention there is a plane wave ultrasonic pulse generator, an ultrasonic wave manipulation device, an ultrasonic detector and an image generator. In a method according to the invention, a biological object is imaged by emitting an unfocussed ultrasonic energy wave front, reflecting at least a portion of the ultrasonic energy wave front from the object, altering a direction of the ultrasonic energy, detecting that energy, and using the detected energy to create an image of the object.

1 Claim, 17 Drawing Sheets

(56) References Cited

U.S. PATENT DOCUMENTS

| | | |
|---|---|---|
| 7,037,268 B1 | 5/2006 | Sleva et al. |
| 7,382,688 B2 | 6/2008 | Miyazaki et al. |
| 7,436,736 B2 | 10/2008 | Schneider et al. |
| 7,739,912 B2 | 6/2010 | Schneider et al. |
| 8,098,915 B2 | 1/2012 | Schneider et al. |
| 8,139,827 B2 | 3/2012 | Schneider et al. |
| 2001/0039836 A1* | 11/2001 | Ogawa ............... 73/608 |
| 2005/0041559 A1 | 2/2005 | Hendriks et al. |
| 2005/0163353 A1 | 7/2005 | Schneider et al. |
| 2008/0197753 A1 | 8/2008 | Schneider et al. |

* cited by examiner

BIOMETRIC SCANNER WITH WAVEGUIDE ARRAY

CROSS-REFERENCE TO RELATED APPLICATION

This application is a continuation of U.S. patent application Ser. No. 11/754,131 (the "'131 Application"), which was filed on May 25, 2007. The '131 Application claims the benefit of priority to U.S. provisional patent application Ser. No. 60/803,150, filed on May 25, 2006 and U.S. provisional patent application Ser. No. 60/822,087, filed on Aug. 11, 2006.

FIELD OF THE INVENTION

The invention relates to an ultrasonic biometric fingerprint reader.

BACKGROUND OF THE INVENTION

Since the 1800's fingerprint information has been collected from human fingers and hands by means of ink and paper. For the purposes of this document, the term fingerprint is used to mean the skin surface friction ridge detail of a single fingerprint, partial fingerprint or any portion of the skin surface friction ridge of up to and including the entire hand. In recent years various electronic fingerprint scanning systems have been developed utilizing optical, capacitance, direct pressure, thermal and ultrasonic methods. Methods based upon ultrasound have proven to be the most accurate, since they are virtually immune to the effects of grease, dirt, paint, ink and other image contaminants.

The ultrasound method employs a piezoelectric transducer that sends a sound wave or pulse through an ultrasonic transmitting media. The pulse is then partially reflected back at each media interface. The reflected pulse is received by the transducer, and the lapsed time between sending and receiving the pulse may be used as a measure of the distance traveled by the pulse going and returning from each reflecting material interface. In order to detect those reflected signals corresponding to the fingerprint, a particular time interval may be monitored. Since the finger is positioned a known distance from the transducer and since the speed of the ultrasound signal is known, the signals reflected from the finger will be expected at the transducer during a particular time interval. This process is called range gating (biasing). The signal received during the particular time interval may be converted to a digital value representing the signal strength. The lapsed time may be displayed graphically to create a contour map of the fingerprint. Often a gray-scale bitmap image is used to graphically display the information.

Although ultrasound imaging of a fingerprint is superior in detail to a similar image collected by an optical system, it takes more time to collect a raster scanned ultrasonic image because common ultrasonic scanning mechanisms often collect each pixel of image information individually by means of a two axis mechanical scanning apparatus. Optical systems usually collect many pixels of information at a single time.

SUMMARY OF THE INVENTION

The invention may be employed to create an image of a biological object, such as the fingerprint of a human finger. In one embodiment of the invention there is a plane wave ultrasonic pulse generator, an ultrasonic wave manipulation device, an ultrasonic detector and an image generator. The generator may be capable of producing an unfocussed ultrasonic energy wave.

The ultrasonic wave manipulation device may alter the direction of at least some of the ultrasonic energy produced by the generator. For example, the wave manipulation device may alter the direction of ultrasonic energy that has been reflected by the object being imaged. The wave manipulation device may be an ultrasonic lens, an ultrasonic mirror or an ultrasonic energy wave guide.

The detector may be positioned to detect ultrasonic energy reflected from the object being imaged and the image generator may be capable of creating an image of the object using the detected ultrasonic energy.

The invention may be embodied as a method of imaging a biological object, such as a finger having a fingerprint. In one such method, an unfocussed ultrasonic energy wave front is emitted and reflected by the finger. The reflected energy may be manipulated so that a direction of the ultrasonic energy is altered, and then detected by a detector. The direction of the ultrasonic energy may be altered by refraction or by reflection, or a combination of both. The detected energy may be used to create an image of the fingerprint using the detected ultrasonic energy.

BRIEF DESCRIPTION OF THE DRAWINGS

For a fuller understanding of the nature and objects of the invention, reference should be made to the accompanying drawings and the subsequent description. Briefly, the drawings are.

The following list may be useful in understanding the figures.

Figure 1:
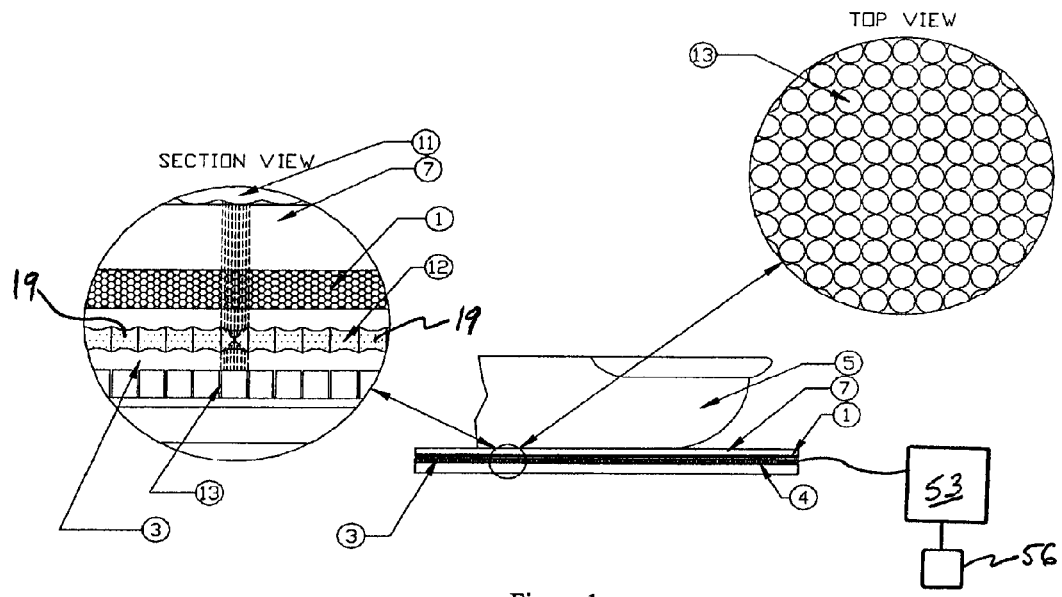
FIG. 1 is a diagram of a fingerprint scanner according to the invention which uses a piezoelectric ultrasonic-plane-wave pulse-generator, an ultrasonic micro-lens array, and an ultrasonic detector array.

1. Piezoelectric plane wave generator
2. Plano-curved lens (may be plano-convex or plano-concave depending upon the material and propagation media properties)
3. Ultrasound transmitting media (e.g. oil, gel, plastisol)
4. Solid state ultrasound receiving detector array
5. Finger
6. Image of the finger (illustrated as a phantom finger image)
7. Imaging platen
8. Reflector (e.g. prism, mirror, or polished flat surface)
9. Ellipsoidal reflector
10. Compound lens assembly
11. Fingerprint ridges
12. Molded ultrasonic micro-lens assembly
13. Detector array elements
14. Curved-lens (may be convex-convex or concave-concave depending upon the material and propagation media properties)
15. Ultrasonic plane wave represented as a ray
16. Ray representation of a plane wave pulse
17. Ray representation of a plane wave echo
18. Ultrasonic beam splitter
19. Lens array elements
20. 45-90-45 prism
21. Plano-curved cylindrical ultrasonic lens assembly.
22. plate array of ultrasonic waveguide elements
25. finger
28. first metallic electrode layer
31. second metallic electrode layer
37. adhesive
38. backing plate
50. image generator
53. computer
56. monitor
160. platen
190. generator
220. piezoelectric film
302. electret film
303. large area electrode
304. small finger-like electrode
307. hydrophone element
310 TFT Hydrophone Array
320 Electret Material
330 Outer Electrode
340 Inner Electrode or Inner Electrode Array
350 Array of TFT FETs
360 Insulating Substrate Base
380 Charge Readout
390 Ultrasonic Image Source
400 Acoustic Array Imager
410 Image Processor Further Description Of The Invention FIG. 1 is a diagram of a scanner that may be used to create an image of a surface of a biological object. In this example, the scanner is a fingerprint scanner. The fingerprint scanner of FIG. 1 has a plane wave generator 1, an ultrasonic detector array 4 suitable for receiving an ultrasonic signal, a wave manipulation device in the form or a micro-lens array assembly 12, and an ultrasonic detector 4. The ultrasonic detector 4 is in communication with an image generator 50, which in this example is a computer 53 having software running thereon for causing the computer 53 to receive signals from the detector 4, interpret those signals as fingerprint information, and display an image of the fingerprint on the monitor 56.

The plane wave generator 1 may be made from a piezoelectric film. Such a generator 1 is described in more detail below, which is attached hereto and made a part of this document.

The ultrasonic detector array 4 may be a hydrophone, or hydrophone array module, examples of which are described below.

The embodiment of the invention that is shown in FIG. 1 has each element 13 of the ultrasonic detector 4 aligned with an individual ultrasonic lens 19. Each lens 19 may refract the ultrasonic energy so as to focus the ultrasonic energy of the reflected plane wave onto an array element 13 to provide improved signal reception by the detector 4.

Such a fingerprint scanner may perform in the following manner. The plane wave generator 1 creates an ultrasonic wave, which emanates from the plane wave generator 1 both toward and away from the platen 7 surface, where the finger 5 is placed. The wave emanating from the generator 1 and traveling away from the platen 7 may be ignored by the detector 4. The wave emanating from the generator 1 and traveling toward the platen 7 reaches the platen 7 where the finger 5 has been placed, and at least some of the ultrasonic energy is reflected back toward the generator 1 by the platen 7 and some of the ultrasonic energy is reflected back toward the generator 1 by the finger 5. At those locations where fingerprint ridges 11 contact the platen 7, some of the ultrasonic energy travels into the finger 5 and some is reflected back. Where no part of the finger touches the platen 7—e.g. where fingerprint valleys are located—some of the ultrasonic energy that passed through the platen 7 will be reflected back once it reaches the surface of the finger 5.

When an ultrasonic pulse reaches the finger, at least some of the ultrasonic energy is reflected back toward the detector 4. The amount of energy reflected back will be different depending upon whether the reflection is caused by a ridge or a valley of the fingerprint. At a valley, all or nearly all of the energy is reflected back, because air is in contact with the platen 7. At a ridge, most of the energy is absorbed by the finger and only a small quantity of ultrasonic energy is reflected back. At the ridge-valley transition region, the energy reflected back will be between these two values. The detector 4 then measures the amount of energy received, and then the computer 53 translates that value into the grey scale image that is displayed on monitor 56.

The waves reflected back, which carry image information about the fingerprint, pass through the plane wave generator 1 where a small portion of the energy may be absorbed, reflected and scattered. Most of the reflected ultrasonic energy continues through the generator 1 toward the ultrasonic detector array 4. Upon reaching the micro-lens assembly 12, each lens 19 focuses the reflected ultrasonic energy onto the associated array element 13. The array element 13 detects the reflected ultrasonic energy and converts it into an electric signal that may be measured and used with the signals from all of the other array elements 13 to create a grey-scale image of the fingerprint.

The platen 7 may be constructed to prevent electrostatic discharge with the detector array elements 13. For example, the platen 7 may a polycarbonate layer approximately 1/32 inch thick. Other suitable materials include acrylic, polystyrene or an insulating plastic material. The platen 7 provides a surface on which a finger may be placed.

A 0.001 inch thick layer of epoxy adhesive may be used to bond the plane wave generator 1 to the platen 7. The plane wave generator 1 may be a 0.001 inch thick layer of piezoelectric material, for example PVDF or PVDF-TrFE copolymer. A 0.001 inch thick layer of epoxy adhesive may be used to bond a 1/32 inch thick second layer of polycarbonate (or acrylic, polystyrene or an insulating plastic material) to the plane wave generator 1.

Figure 2:
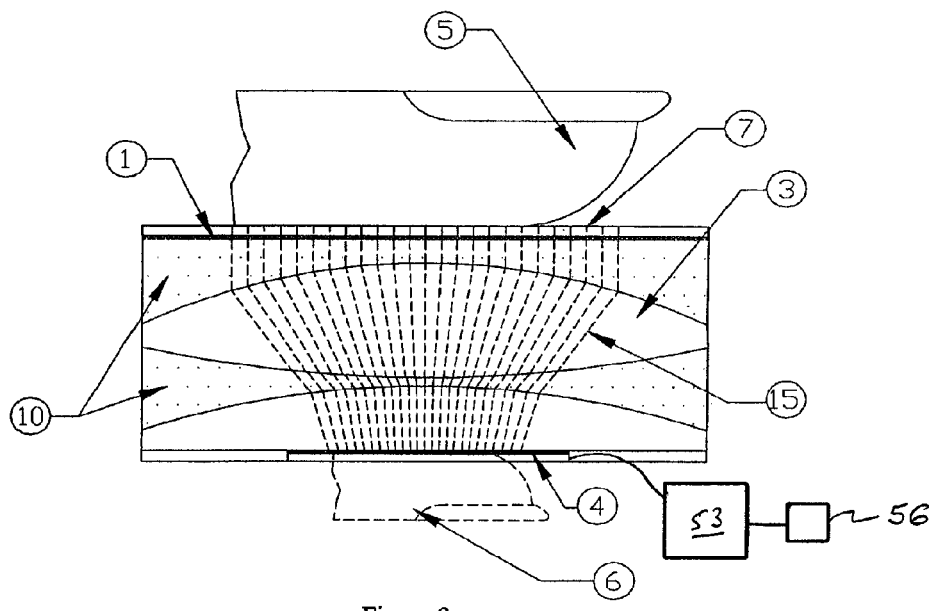
FIG. 2 is a diagram of a fingerprint scanner according to the invention which uses a piezoelectric ultrasonic-plane-wave pulse-generator, a compound lens assembly, and an ultrasonic detector array.

FIG. 2 depicts an embodiment of the invention in which a fingerprint scanner uses a plane wave generator 1, an ultrasonic detector array 4 suitable for receiving an ultrasonic signal, and a wave manipulation device, which in this embodiment is a compound lens assembly 10 that transfers the reflected ultrasonic energy to the ultrasonic detector array 4. In the embodiment depicted in FIG. 2, the first lens 2 is plano-concave and the second lens 2 is concave-concave. The lenses of the assembly 10 may be made from a material such as polystyrene, acrylic resin or silicone rubber.

In the embodiment depicted in FIG. 2, (as in the device of FIG. 1) a plane wave pulse may be generated by the plane wave generator 1, and the pulse may travel toward the platen 7 and finger 5. Upon reaching the platen 7 and finger 5, ultrasonic energy may be reflected back. The reflected energy travels back through the plane wave generator 1 and the transmission media 3. The compound lens system 10 shapes the reflected energy and directs it toward the ultrasonic detector array 4 where it is received at each element 13. The image information from each array element 13 may be used to create a two dimensional grey-scale image 6 of the fingerprint. Although the image 6 is depicted in FIG. 2 as being on the detector 4, this is done merely to illustrate the orientation of the image 6 in relation to the orientation of the finger 5—the image 6 will normally be presented on a device that is distant from the detector 4, such as on the monitor 56. Having shown the computer 53 and monitor 56 in two figures, it will be understood that the computer 53 and monitor 56 may be connected to the detector 4 in the other embodiments of the invention, and so the computer 53 and monitor 56 will not be repeatedly illustrated in the other figures, even though it will be understood that these devices may be used in the embodiments illustrated in those other figures.

Figure 3:
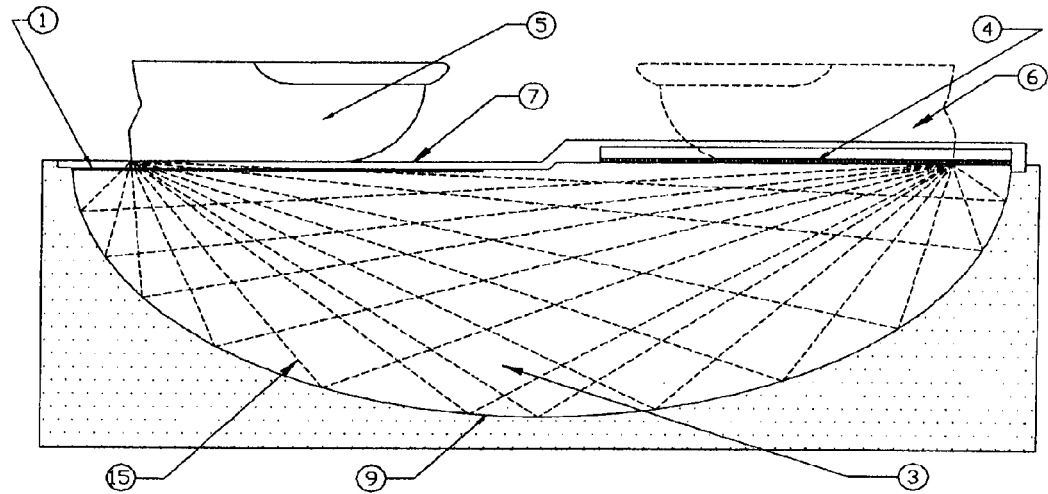
FIG. 3 is a diagram of a fingerprint scanner according to the invention which has a piezoelectric ultrasonic-plane-wave pulse-generator, an ellipsoidal ultrasonic mirror that transfers the reflected pulse from one focal point of the ellipsoid to an array of ultrasonic detectors located at the second focal point of the ellipsoid.

FIG. 3 shows an embodiment of the invention in which a fingerprint scanner uses a plane wave generator 1, an ultrasonic detector array 4 suitable for receiving an ultrasonic signal, and a wave manipulation device, which in this embodiment is an ellipsoidal reflector 9 that reflects the ultrasonic energy that was reflected by the finger 5 to the ultrasonic detector array 4. The reflector 9 may be a polished polystyrene surface or a metallized surface. The reflector 9 may also be polished glass, acrylic, aluminum, or steel.

In the embodiment depicted in FIG. 3, a plane wave pulse is generated by the plane wave generator 1. The pulse travels toward the platen 7 and finger 5, which is located at one of the ellipsoid's focal points. Upon reaching the platen 7, some of the ultrasonic energy may be reflected back while some travels into the finger. Additionally some of the energy may be scattered. The reflected energy, for example the energy reflected by the valleys of the fingerprint, travels back through the plane wave generator 1 and the transmission media 3. The ellipsoidal reflector 9 reflects the ultrasonic energy that passed through the generator 1 to the ultrasonic detector array 4, which is located at the ellipsoid's second focal point, where the reflected energy is received by the detector array 4. Signals from the detector array 4 correspond to the energy received, and may be used to create a two dimensional grey-scale image 6 of the fingerprint. Although the image 6 is depicted in FIG. 3 as being on the detector 4, this is done merely to illustrate the orientation of the image 6 in relation to the orientation of the finger 5—the image 6 will normally be presented on a device that is distant from the detector 4, such as on the monitor 56.

Figure 4:
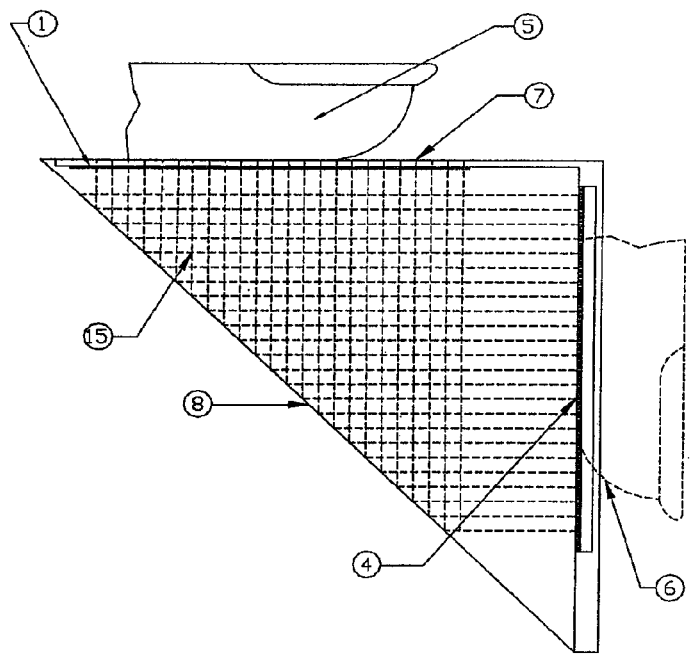
FIG. 4 is a diagram of a fingerprint scanner according to the invention which has a piezoelectric ultrasonic-plane-wave pulse-generator and an ultrasonic mirror to reflect an ultrasonic pulse to an ultrasonic detector array.

FIG. 4 shows an embodiment of the invention in which a fingerprint scanner uses a plane wave generator 1, an ultrasonic detector array 4 suitable for receiving an ultrasonic signal, and a wave manipulation device, which in this embodiment is a substantially flat surface reflector 8 that may be a surface of a prism. The prism may be made from a material such as polystyrene, acrylic resin or silicone rubber. The reflector 8 transfers the ultrasonic energy that was reflected by the finger 5 to the ultrasonic detector array 4. In this embodiment a plane wave pulse is generated by the plane wave generator 1. The pulse travels toward the platen 7 and finger 5. Upon reaching the finger 5, some of the ultrasonic energy may be reflected back while some travels into the finger. Additionally some of the energy may be scattered. The reflected energy travels back through the plane wave generator 1 and the transmission media 3. The reflector 9 transfers the ultrasonic energy to ultrasonic detector array 4. The signals from each array element 13 of the detector 4 may be used to create a two dimensional grey-scale image 6 of the fingerprint. Although the image 6 is depicted in FIG. 4 as being on the detector 4, this is done merely to illustrate the orientation of the image 6 in relation to the orientation of the finger 5—the image 6 will normally be presented on a device that is distant from the detector 4, such as on the monitor 56.

It should be noted that the embodiment of FIG. 4 has the generator 1 oriented substantially at right angles to the detector 4. Other embodiments of the invention are shown herein (see FIGS. 9, 10, 15 and 16) with the generator 1 and the detector 4 oriented substantially at right angles to each other.

Figure 5:
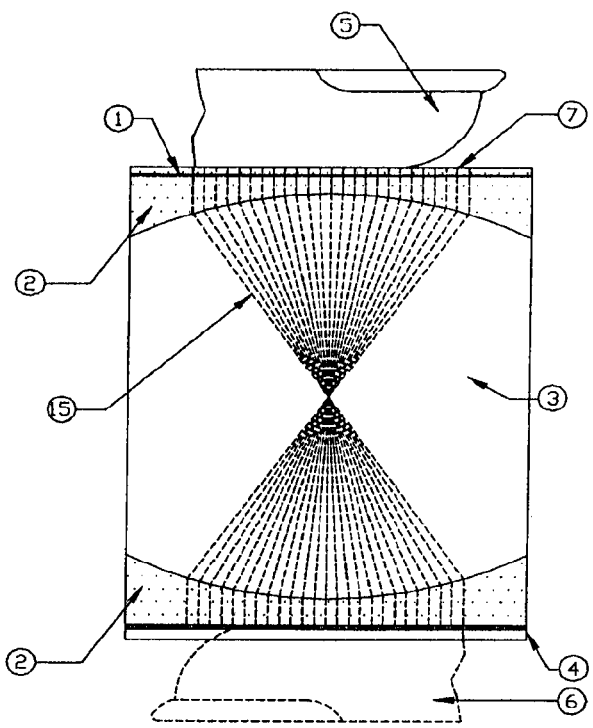
FIG. 5 is a diagram of a fingerprint scanner according to the invention which has a piezoelectric ultrasonic-plane-wave pulse-generator, two plano-concave lenses, and an ultrasonic detector array.

FIG. 5 shows an embodiment of the invention in which a fingerprint scanner uses a plane wave generator 1, an ultrasonic detector array 4 suitable for receiving an ultrasonic signal, and a wave manipulation device, which in this embodiment is a pair of matched ultrasonic lenses 2. The lenses 2 may be made from a material such as polystyrene, acrylic resin or silicone rubber. It will be recognized that the lenses 2 will manipulate the ultrasonic energy reflected by the finger 5 so as to produce an inverted image, once the computer 53 processes the signals received from the detector 4. In this embodiment a plane wave pulse may be generated by the plane wave generator 1. The pulse travels toward the platen 7 and finger 5. Upon reaching the platen imaging surface 7, some of the ultrasonic energy may be reflected back while some travels into the fingerprint ridges and finger. Additionally some of the energy may be scattered. The reflected energy travels back through the plane wave generator 1 and the transmission media 3. A first plano-curved lens 2 shapes the reflected energy pulse and directs it through the media 3 toward a second plano-curved lens 2 where the wave (represented by rays) is re-collimated before going on to the ultrasonic detector 4 where it is received at each element 13. The image information from each array element 13 may be used to create a two dimensional grey-scale image 6 of the fingerprint. Although the image 6 is depicted in FIG. 5 as being on the detector 4, this is done merely to illustrate the orientation of the image 6 in relation to the orientation of the finger 5—the image 6 will normally be presented on a device that is distant from the detector 4, such as on the monitor 56.

Figure 6:
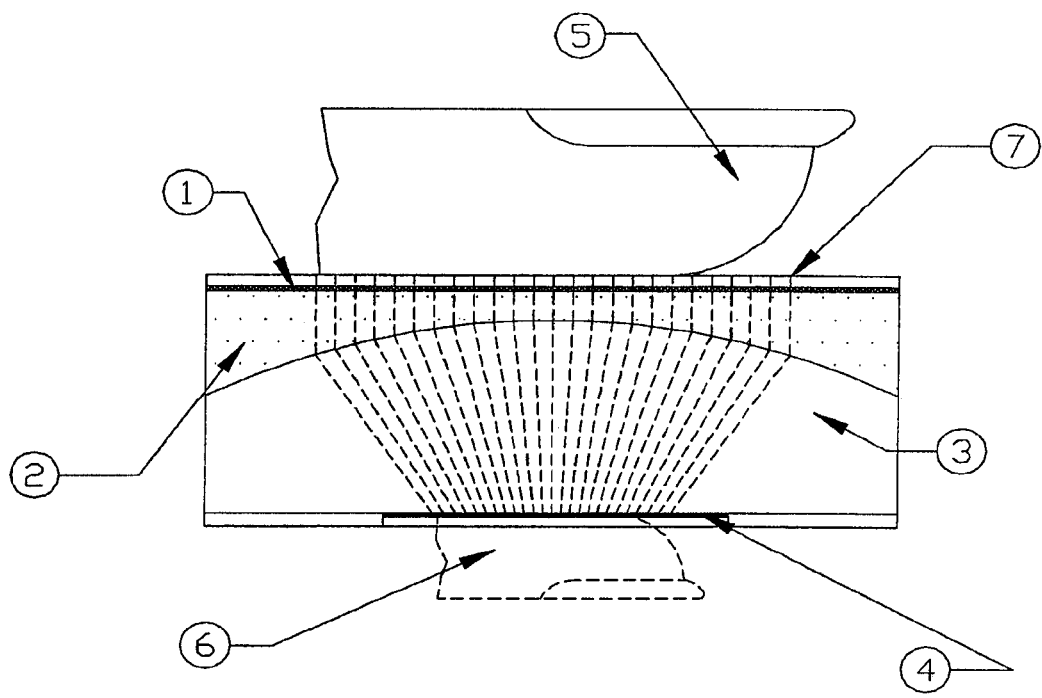
FIG. 6 is a diagram of a fingerprint scanner according to the invention which has a piezoelectric ultrasonic-plane-wave pulse-generator and a plano-concave lens to transfer a reflected ultrasonic pulse to an ultrasonic detector array.

FIG. 6 shows an embodiment of the invention in which a fingerprint scanner uses a plane wave generator 1, an ultrasonic detector 4 suitable for receiving and detecting ultrasonic energy, and a wave manipulation device, which in this embodiment is a single ultrasonic lens 2 that may be used to focus the ultrasonic energy onto an ultrasonic detector array 4 that is smaller than the finger 5. The lens 2 may be made from a material such as polystyrene, acrylic resin or silicone rubber. In this embodiment of the invention, a plane wave pulse may be generated by the plane wave generator 1. The pulse travels toward the platen 7 and finger 5. Upon reaching the platen imaging surface 7, some of the ultrasonic energy may be reflected back while some travels into the fingerprint ridges and finger. Additionally some of the energy may be scattered. The reflected energy travels back through the generator 1 and the transmission media 3. A plano-curved lens 2 shapes the pulse and directs it toward the ultrasonic detector array 4 where it is received at each element 13. The signals generated by the elements 13 may be used by the computer 53 to create a two dimensional grey-scale image 6 of the fingerprint. Although the image 6 is depicted in FIG. 6 as being on the detector 4, this is done merely to illustrate the orientation of the image 6 in relation to the orientation of the finger 5—the image 6 will normally be presented on a device that is distant from the detector 4, such as on the monitor 56.

Figure 7:
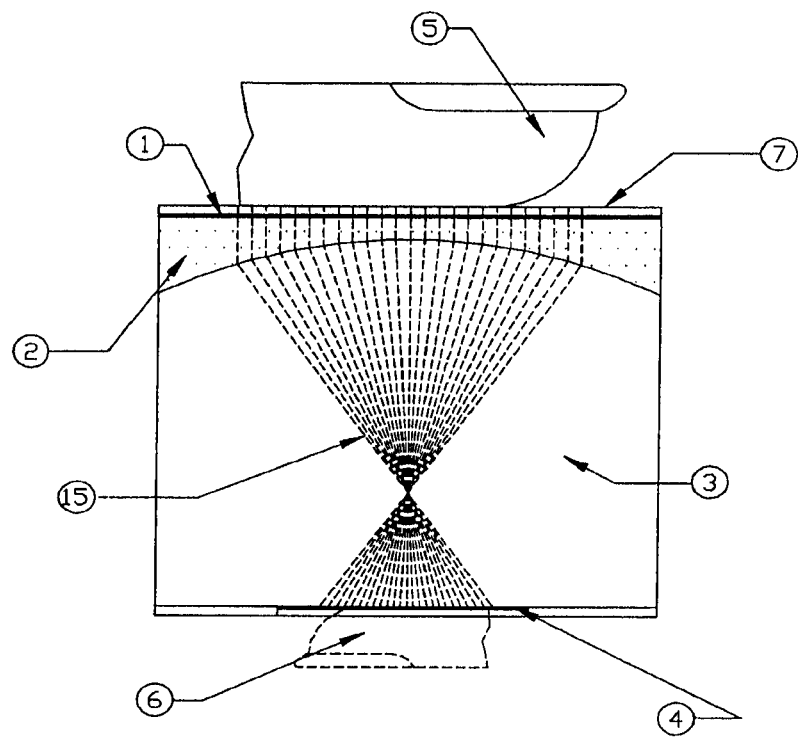
FIG. 7 is a diagram of a fingerprint scanner according to the invention which has a piezoelectric ultrasonic-plane-wave pulse-generator and a plano-concave lens to transfer a reflected ultrasonic pulse to an ultrasonic detector array.

FIG. 7 shows an embodiment of the invention which is similar to that shown in FIG. 6. However, unlike the embodiment of FIG. 6, in the embodiment depicted in FIG. 7 the ultrasonic energy received at the detector 4 will produce an inverted image because the detector 4 is located beyond the focal point of the lens 2. In this embodiment a plane wave pulse is generated by the plane wave generator 1. The pulse travels toward the platen 7 and finger 5. Upon reaching the platen imaging surface 7, some of the ultrasonic energy may be reflected back while some travels into the fingerprint ridges and finger 5. Additionally some of the energy may be scattered. The reflected energy travels back through the plane wave generator 1 and the transmission media 3. A plano-curved lens 2 shapes the pulse and directs it toward the ultrasonic detector array 4 where it is received at each element 13. The image information from each array element 13 may be used to create a two dimensional grey-scale image 6 of the fingerprint. Although the image 6 is depicted in FIG. 7 as being on the detector 4, this is done merely to illustrate the orientation of the image 6 in relation to the orientation of the finger 5—the image 6 will normally be presented on a device that is distant from the detector 4, such as on the monitor 56.

Figure 8:
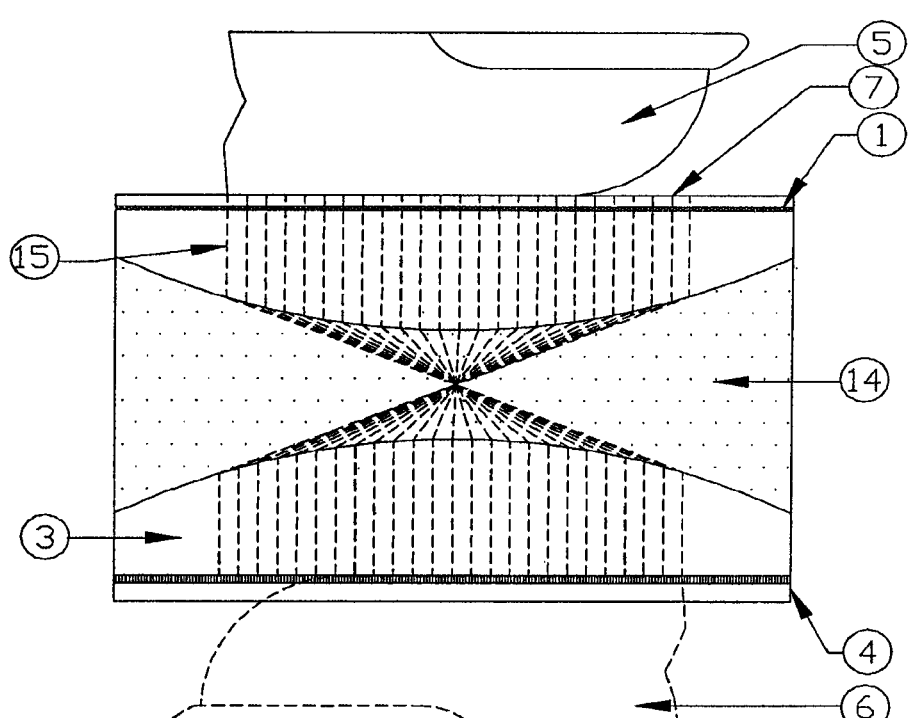
FIG. 8 is a diagram of a fingerprint scanner according to the invention which has a piezoelectric ultrasonic-plane-wave pulse-generator and a concave-concave lens to transfer a reflected ultrasonic pulse to an ultrasonic detector array.

FIG. 8 shows an embodiment of the invention in which a fingerprint scanner uses a plane wave generator 1, an ultrasonic detector array 4 suitable for receiving ultrasonic energy, and a wave manipulation device, which in this embodiment is a single ultrasonic lens 14 that is not flat on either side. The lens depicted in FIG. 8 is a convex-convex lens. The lens 14 may be made from a material such as polystyrene, acrylic resin or silicone rubber. The lens 14 may be used to focus the reflected ultrasonic energy onto an ultrasonic detector array 4 while inverting the fingerprint image 6. In this embodiment a plane wave pulse is generated by the plane wave generator 1. The pulse travels toward the platen 7 and finger 5. Upon reaching the platen imaging surface 7, some of the ultrasonic energy may be reflected back while some travels into the fingerprint ridges and finger 5. Additionally some of the energy may be scattered. The reflected energy travels back through the plane wave generator 1 and the transmission media 3. A double-curved lens 14 shapes the pulse and directs it toward the ultrasonic detector 4 where it is received at each element 13. The image information from each array element 13 may be used to create a two dimensional grey-scale image 6 of the fingerprint. Although the image 6 is depicted in FIG. 8 as being on the detector 4, this is done merely to illustrate the orientation of the image 6 in relation to the orientation of the finger 5—the image 6 will normally be presented on a device that is distant from the detector 4, such as on the monitor 56.

Figure 9:
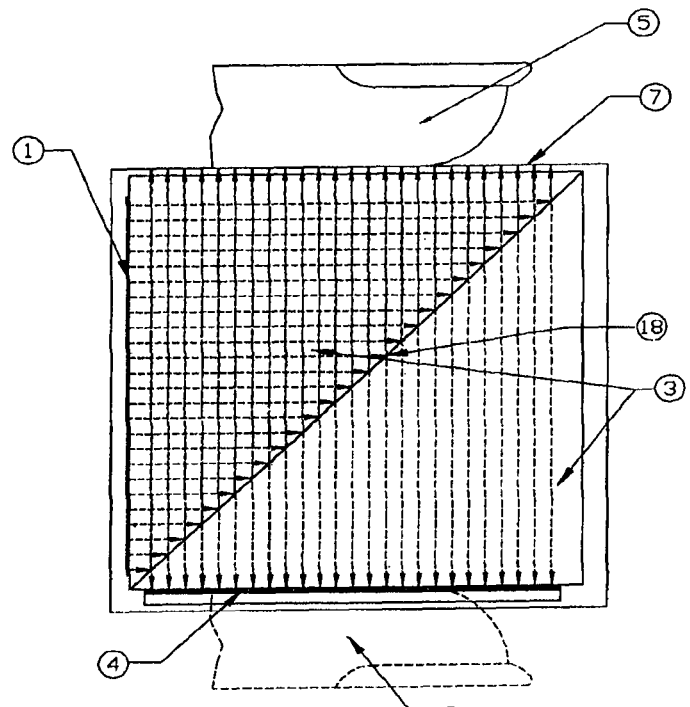
FIG. 9 is a diagram of a fingerprint scanner according to the invention which has a piezoelectric ultrasonic-plane-wave pulse-generator and a pulse splitter that reflects ultrasonic energy toward the platen and finger where the pulse is reflected back toward the splitter, and some of the reflected pulse passes through the splitter to continue toward and be received by the ultrasonic detector array.

FIG. 9 shows an embodiment of the invention in which a fingerprint scanner uses a plane wave generator 1, an ultrasonic detector array 4 suitable for receiving an ultrasonic signal, and a wave manipulation device, which in this embodiment is a splitter 18 that is partially reflective and partially transmissive, so that some of the ultrasonic energy impacting the splitter 18 may be reflected toward the platen 7 and finger 5, and so that some of the ultrasonic energy reflected from the finger is allowed to pass through the splitter 18 and continue on to the ultrasonic detector array 4. The splitter may be formed from a material such as paper or mylar. In this embodiment a plane wave pulse is generated by the plane wave generator 1. The pulse travels toward the splitter 18. The splitter 18 reflects a portion of the ultrasonic energy from the pulse toward the platen 7 and finger 5. Some of the ultrasonic energy received by the finger 5 may be reflected back while some travels into the fingerprint ridges and finger. Additionally some of the energy may be scattered. The reflected energy travels back and passes through the splitter 18 and the transmission media 3. After passing through the splitter 18, the reflected energy continues toward the ultrasonic detector array 4 where it is received at each element 13. The image information from each array element 13 may be used to create a two dimensional grey-scale image 6 of the fingerprint. Although the image 6 is depicted in FIG. 9 as being on the detector 4, this is done merely to illustrate the orientation of the image 6 in relation to the orientation of the finger 5—the image 6 will normally be presented on a device that is distant from the detector 4, such as on the monitor 56.

Figure 10:
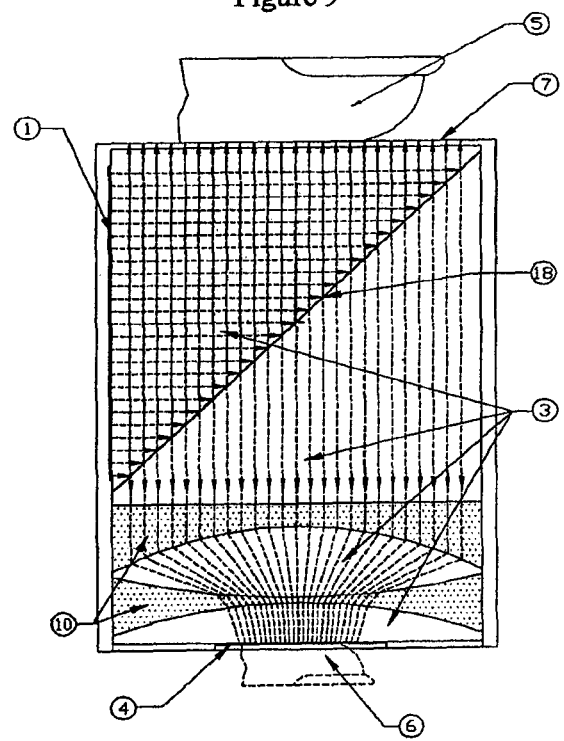
FIG. 10 is a diagram of a fingerprint scanner according to the invention which has a piezoelectric ultrasonic-plane-wave pulse-generator and a pulse splitter that reflects the ultrasonic pulse toward the platen and finger where the pulse is reflected back toward the splitter, and some of the reflected pulse passes through the splitter to continue toward and be received by the ultrasonic detector array, which is physically smaller than the area of the finger, and an ultrasonic lens system focuses the reflected pulse on the ultrasonic detector array.

FIG. 10 shows a modified version of the fingerprint scanner shown in FIG. 9. In this embodiment an ultrasonic compound lens assembly 10 may be used to focus the ultrasonic energy onto the ultrasonic detector array 4. The lens assembly 10 may be made from a material such as polystyrene, acrylic resin or silicone rubber. This arrangement may be used if the ultrasonic detector array 4 is smaller than the area of the finger 5 that is required for imaging.

Figure 11A:
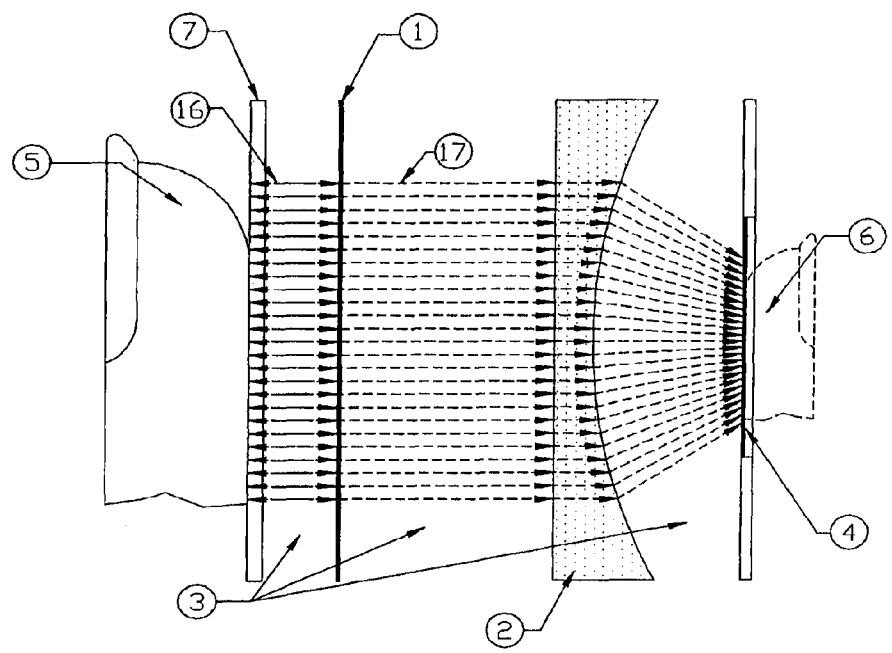
FIGS. 11A and 11B are diagrams of a fingerprint scanner according to the invention illustrating how an image of an object may be transferred from the platen surface to the ultrasonic detector array.
Figure 11B:
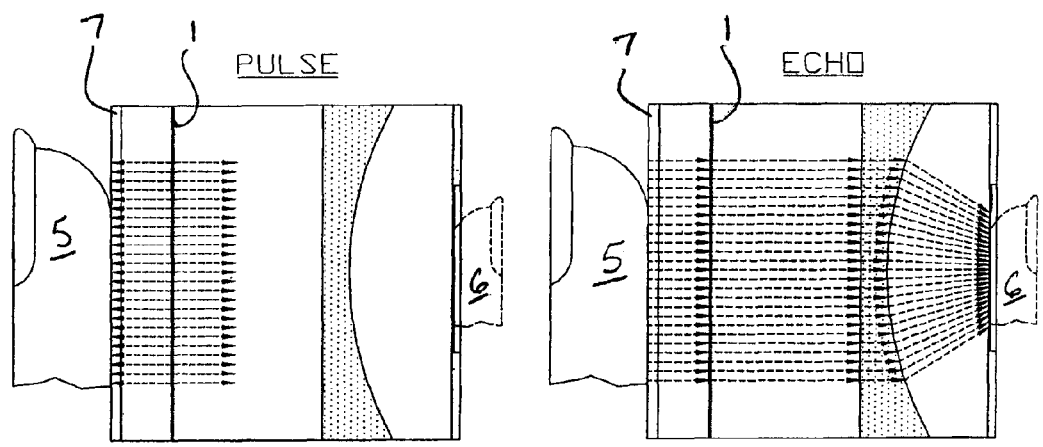
Figure 12:
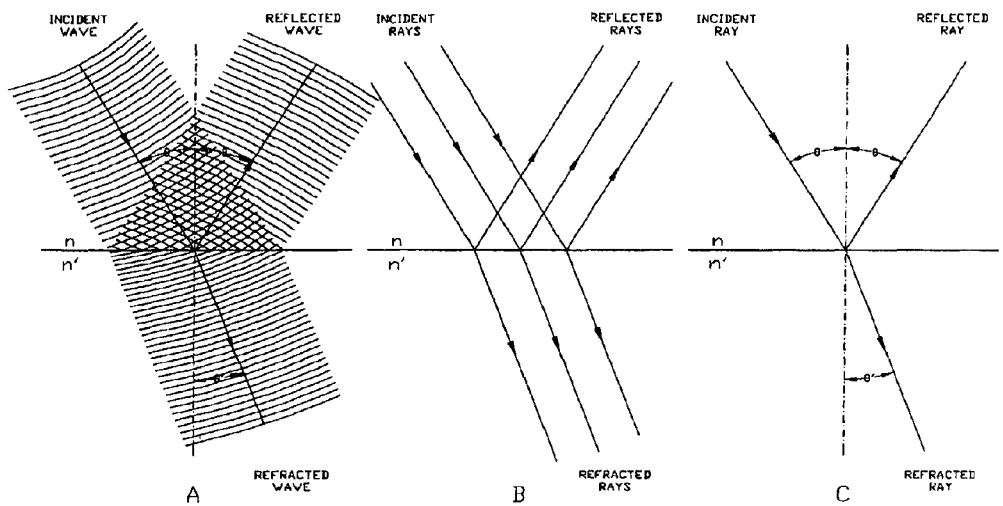
FIG. 12 is a diagram depicting the "Wave" and "Ray" methods of illustrating optic and ultrasonic systems, and it should be noted that ultrasonic systems obey Snell's Law.

FIGS. 11A and 11B are simplified diagrammatic versions of a fingerprint scanner according to the invention, and these figures may be used to illustrate aspects of some of the embodiments described herein. The plane wave pulse generator 1 creates an ultrasonic pulse 16. The ultrasonic pulse 16 travels through the transmission media 3 to the platen 7 where it continues to the platen 7 and finger 5. Fingerprint ridges in contact with the platen 7 allow some of the ultrasonic energy to continue into the finger, some to be scattered, and some to be reflected. The valleys of the fingerprint will also reflect some of the ultrasonic energy. The reflected ultrasonic energy is shown as feature 17 in FIG. 11A. The reflected energy travels back and passes through the plane wave generator 1 continuing on to the wave manipulation device (in this case a lens 2) that alters the direction of the ultrasonic energy, for example by reflection or by refraction depending upon the devices used. Finally the reflected energy is received by the ultrasonic detector 4 and may be converted into an image 6 of the finger surface. Although the image 6 is depicted in FIGS. 11A and 11B as being on the detector 4, this is done merely to illustrate the orientation of the image 6 in relation to the orientation of the finger 5—the image 6 will normally be presented on a device that is distant from the detector 4, such as on the monitor 56.

FIG. 11B shows two cycles of the operation of the system. In the pulse cycle, the plane wave is generated and travels in both directions away from the plane wave generator 1. In the echo cycle the wave is shown reflected from the finger 5, passing through the plane wave generator 1, being modified by the lens system 2 and finally arriving at the ultrasonic detector 4 to be processed into a grey-scale image 6.

Figure 13:
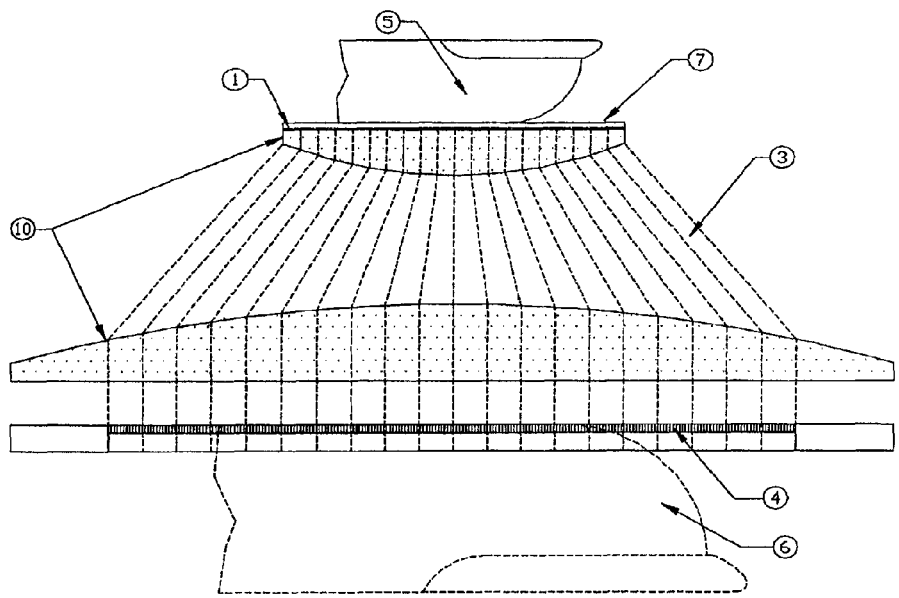
FIG. 13 is a diagram of a fingerprint scanner according to the invention which has a piezoelectric ultrasonic-plane-wave pulse-generator and a compound lens assembly to transfer and enlarge the reflected pulse in order to produce an enlarged fingerprint image.

There may be situations in which increased resolution may be required, but where manufacturing considerations limit the size of the detector array element. In those situations, it may be necessary to enlarge the image of the object that is in contact with the platen. In this case, the detector may be manufactured larger than the object being imaged, and a lens system may be used to expand the reflected energy i.e. enlarge the footprint of the energy. Such a system is shown in FIG. 13. In FIG. 13, the lens assembly 10 has plano-convex lenses.

Figure 14:
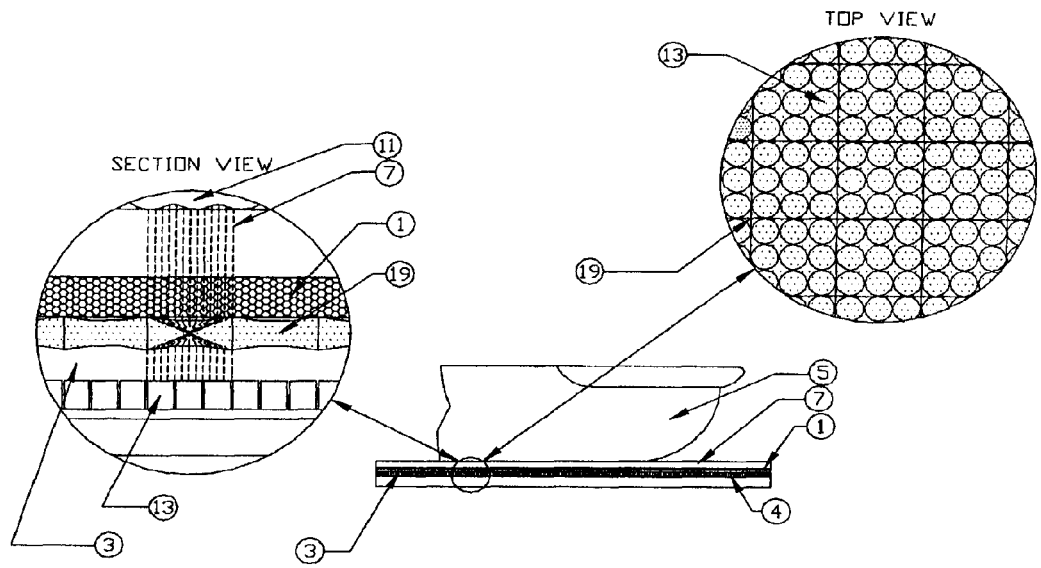
FIG. 14 is a diagram of a fingerprint scanner according to the invention which has a piezoelectric ultrasonic-plane-wave pulse-generator and an ultrasonic lens array to transfer a reflected pulse to an ultrasonic detector array. This embodiment is similar to that of FIG. 1 but the lens array elements are larger in size than a single pixel, and each lens element of the array transfers an image that is received by a group of detector elements.

FIG. 14 shows an embodiment of the invention similar to that of FIG. 1, but in this embodiment the lens array elements 19 are larger than the elements 13 of the detector 4, and energy emanating from a particular elements 19 may impact multiple detector elements 13. In operation each lens array element 19 transfers reflected ultrasonic energy to a group of detector elements 13, instead of individual detector elements 13. Use of such a lens array allows for shorter image transfer distances.

Figure 15:
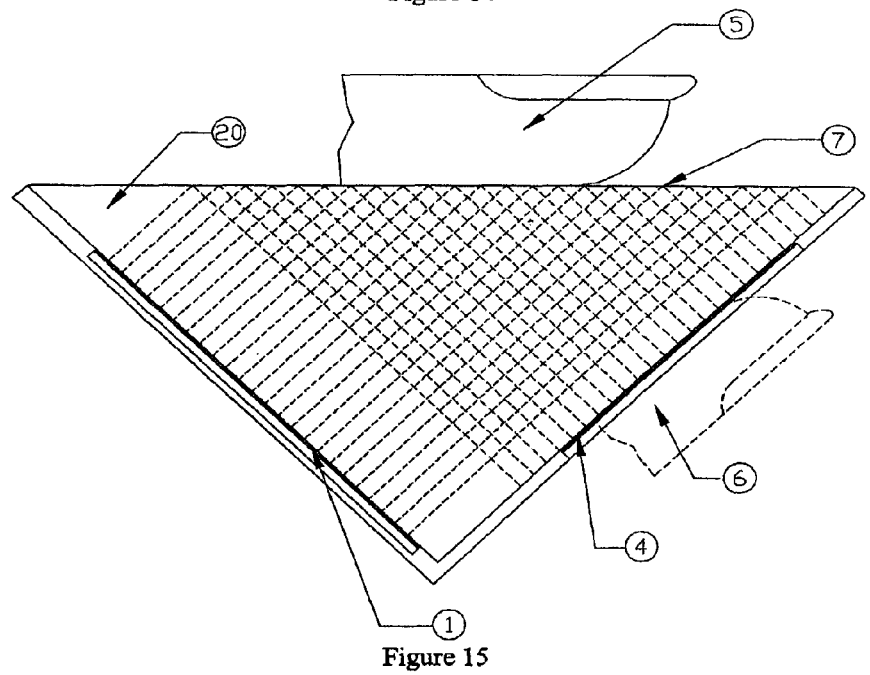
FIG. 15 is a diagram of a fingerprint scanner according to the invention which has a piezoelectric ultrasonic-plane-wave pulse-generator and a 45-90-45 right angle prism. This configuration makes use of frustrated total internal reflection ("FTIR") to obtain a reflected ultrasonic pulse. The image platen is the long dimension side of the prism.

FIG. 15 shows an embodiment of the invention in which the plane wave pulse generator 1 and the piezoelectric detector 4 are mounted to the right angle surfaces of a 45-90-45 prism 20 and the ultrasonic energy may be transferred using frustrated total internal reflection ("FTIR") with the finger platen constituting the long-dimension side of the prism 20. It should be noted that the FTIR image received at the detector 4 will be 70.7% of its original size in one direction (in the plane of the diagram shown) and will be its original size in the other dimension (perpendicular to the diagram shown).

Figure 16:
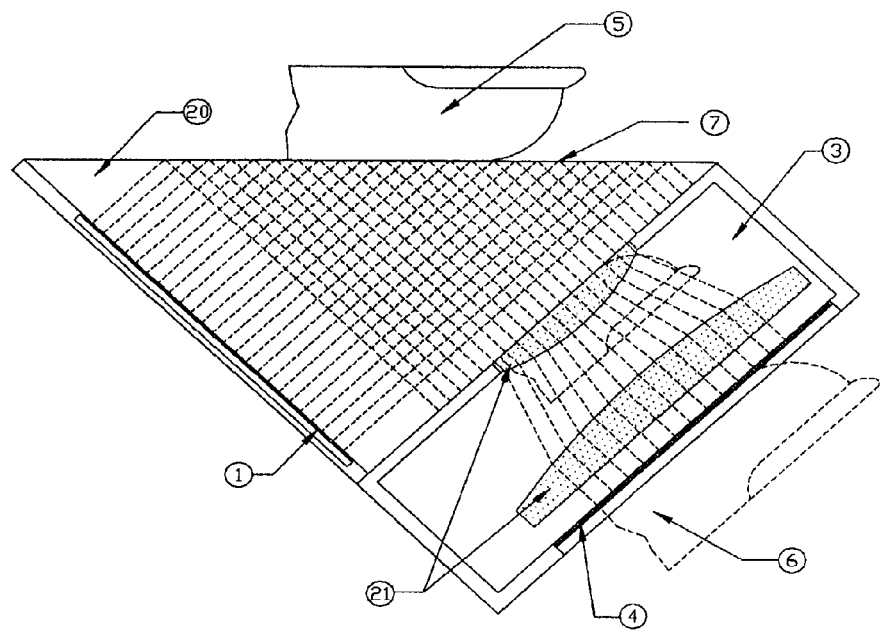
FIG. 16 is a diagram of a fingerprint scanner similar to that depicted in FIG. 15 except that in FIG. 16 there is a compound ultrasonic lens assembly, which may be a compound cylindrical lens assembly to substantially restore the reflected image to its original dimensions.

FIG. 16 depicts an embodiment of the invention similar to that of FIG. 15, but an ultrasonic compound cylindrical lens system 21, mounted with the axis of the cylinder parallel to the parallel vertex lines of the prism 20, is used to restore the image aspect ratio back to a 1:1 ratio.

Figure 17:
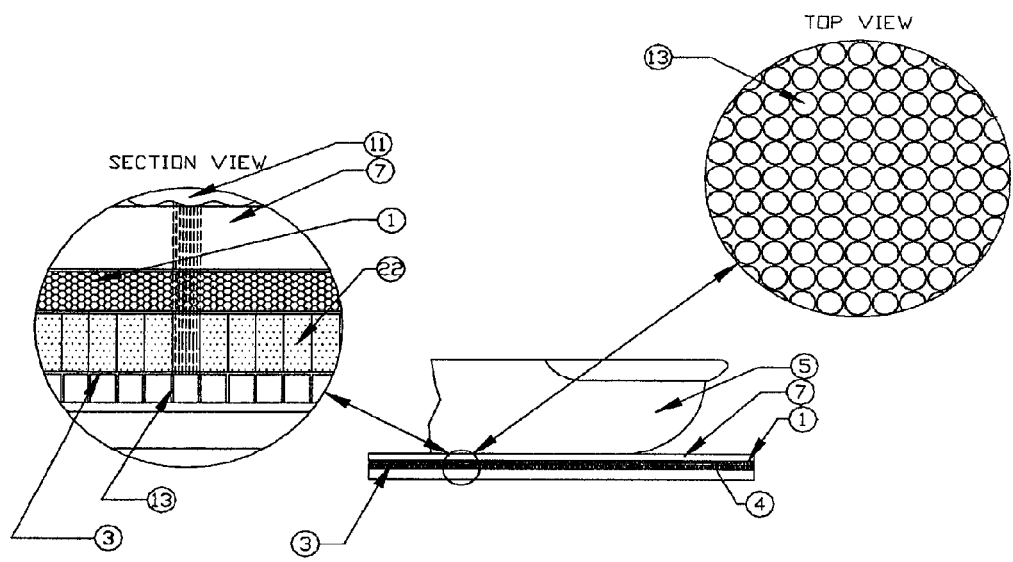
FIG. 17 is a diagram of a fingerprint scanner according to the invention which has a piezoelectric ultrasonic-plane-wave pulse-generator and an ultrasonic fiber waveguide array to transfer a fingerprint image to an ultrasonic detector array.

FIG. 17 shows an embodiment of the invention in which a fingerprint scanner uses a plane wave generator 1, an ultrasonic detector array 4 suitable for receiving an ultrasonic signal, and a plate array 22 of ultrasonic waveguide elements. The ultrasonic fiber plate may be similar in construction to a photonic type fiber optics plate. Many fibers may be bundled together and fused, bonded or potted so that they have substantially the same orientation. Once bundled, the fibers may be sliced perpendicular to the fibers into sheets of the thickness needed to form the plate.

The individual fibers may be constructed by creating a cylinder of the core material selected for its ultrasound transmission qualities. The core then may be clad with another material having a substantially lower speed of sound. The cylinder of core and cladding may be heated to soften the core and cladding, and drawn out until the desired diameter is obtained. This creates an ultrasonic fiber which uses total internal reflection to guide ultrasonic energy from one end of the fiber to another end of the fiber. In one particular embodiment where a resolution of 500 dots per inch is needed, each fiber has a diameter of about 0.002 inches, which is comprised of a 0.0015 inch diameter core of polystyrene and a 0.00025 inch thick cladding of acrylic or glass. Each fiber of the plate array uses internal reflection to prevent the ultrasonic energy from spreading, and in this manner alters the direction of the ultrasonic energy.

In the embodiment depicted in FIG. 17, upon reaching the ultrasonic waveguide fiber array 22, each fiber guides the ultrasonic energy onto the corresponding array element 13. Each of the array elements 13 detects the ultrasonic energy and converts it into an electric signal that may be measured and used with the signals from all of the other array elements 13 to create a grey-scale image of the fingerprint.

In the embodiment depicted in FIG. 17 there is a platen 7 on which the finger is positioned. The platen 7 may be 1/32 to 3/32 inches thick. In a variation of this embodiment, the platen is a plastic layer approximately 0.005 to 0.010 inches thick. A 0.001 inch thick layer of epoxy adhesive may be used to bond the plane wave generator 1 to the platen 7. A 0.001 inch thick layer of epoxy adhesive may be used to bond an ultrasonic fiber plate 22 to the plane wave generator 1.

Figure 18:
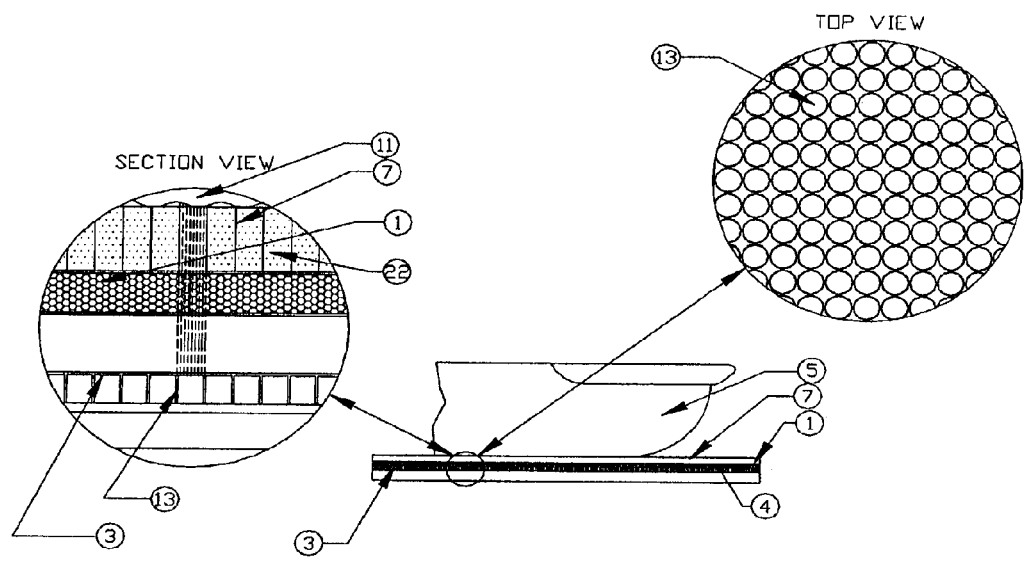
FIG. 18 is a diagram of a fingerprint scanner according to the invention which has a piezoelectric ultrasonic-plane-wave pulse-generator and an ultrasonic fiber waveguide array that is integral to the platen in order to facilitate transfer of the ultrasonic pulse to an ultrasonic detector array.

FIG. 18 is a diagram of a fingerprint scanner according to the invention, which uses a plane wave generator 1, an ultrasonic detector array 4 suitable for receiving an ultrasonic signal, and a plate array 22 of ultrasonic waveguide elements. Each array element 13 of the ultrasonic detector 4 may be aligned with an element of the ultrasonic waveguide array 22, which conducts the ultrasonic energy from the plane wave generator 1 onto an array element 13 to provide maximum signal reception. Such a fingerprint scanner may perform in the following manner. The plane wave generator 1 may create an ultrasonic wave of the ultrasonic frequency necessary for the system. The wave may emanate from the plane wave generator 1 both toward and away from the platen 7 surface where the finger 5 is placed. The wave emanating from the generator 1 and traveling away from the platen 7 may be ignored by the detector 4. The wave emanating from the generator 1 and traveling toward the platen 7 may be guided by the plate array 22 of ultrasonic waveguide fibers, which may be an integral part of the platen 7 on which the finger 5 has been placed. Some of the ultrasonic energy is reflected back by the finger, and this reflected energy passes through the plane wave generator 1 where a small portion of the energy may be absorbed, reflected and scattered. Most of the ultrasonic energy continues on toward the ultrasonic detector 4. Each array element 13 of the detector 4 detects the ultrasonic energy and converts it into an electrical signal that may be measured and may be used with the signals from all of the other array elements to create a grey-scale image of the fingerprint.

Figure 19:
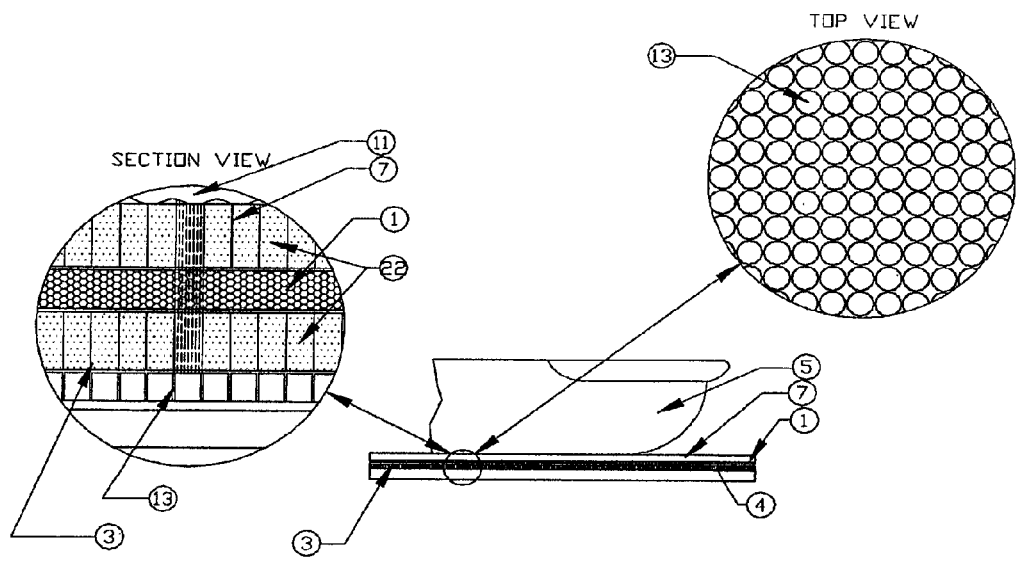
FIG. 19 is a diagram of a fingerprint scanner according to the invention which has a piezoelectric ultrasonic-plane-wave pulse-generator and two ultrasonic fiber waveguide array plates that sandwich the generator and facilitate transfer of the ultrasonic pulse to an ultrasonic detector array.

FIG. 19 is a diagram of a fingerprint scanner according to the invention, which uses a plane wave generator 1, an ultrasonic detector array 4 suitable for receiving an ultrasonic signal, and a plate array of ultrasonic waveguide elements 22. Each array element 13 of the ultrasonic detector array 4 may be aligned with an individual ultrasonic lens that focuses the ultrasonic energy from the plane wave onto the array element 13 to provide maximum signal reception. Such a fingerprint scanner may perform in the following manner. The plane wave generator 1 may create an ultrasonic wave of the ultrasonic frequency necessary for the system. The wave may emanate from the plane wave generator 1 both toward and away from the platen 7. The wave emanating from the generator 1 and traveling away from the platen 7 may be ignored by the detector 4. The wave emanating from the generator 1 and traveling toward the platen 7 reaches the platen 7 where the finger 5 has been placed. Upon reaching the finger 5, some of the ultrasonic energy may be reflected back and through the plane wave generator 1, and on to a second ultrasonic waveguide plate array toward the ultrasonic detector array 4. The individual ultrasonic waveguide fibers of the ultrasonic waveguide fiber array 22, guide the ultrasonic energy onto the corresponding array element 13. The array element 13 detects the ultrasonic energy and converts it into an electric signal that may be measured and used with the signals from all of the other array elements to create a grey-scale image of the fingerprint.

A plane wave generator 1, an ultrasonic detector array 4 and an ultrasonic manipulation device that transfers the ultrasonic image information of a biological object in contact with the imaging platen 7 surface to the ultrasonic detector array 4 may be used to obtain information about an object that is in contact with the platen, and the information may be used to generate an image of the object. Although the invention has been described in conjunction with a fingerprint scanner or reader, the invention can be used in other applications which seek to create an ultrasonic image of an object.

Figure 20:
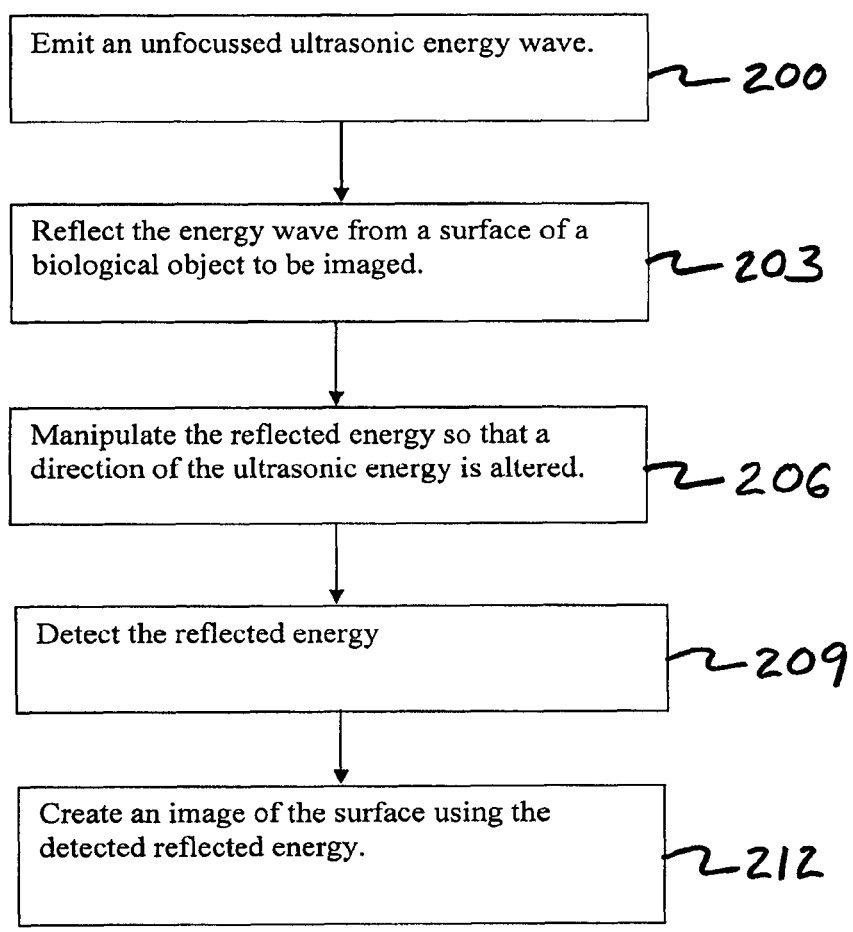
FIG. 20 is a flow chart depicting a method according to the invention.

Having described many devices which embody the invention, it will be recognized that the invention may be embodied as a method of creating an image of a biological object having a surface to be imaged. For example, the biological object may be a finger and the surface may be the friction ridge surface (fingerprint) of the finger. FIG. 20 depicts one such method in which an unfocussed ultrasonic energy wave front is emitted 200, and at least some of the energy wave front is reflected 203 by the biological object. For example, the valleys of a fingerprint may reflect the ultrasonic energy. The reflected energy is manipulated 206 so that a direction of the ultrasonic energy is altered, and then that reflected energy is detected 209. The direction of the energy may be altered by refraction (such as by an ultrasonic lens) or reflected (such as by an ultrasonic mirror or waveguide), or a combination of refraction and reflection. An image may then be created 212 using the detected energy. Devices for creating the image from the detected energy are well known, and will not be described in detail in this document. However, one such device is disclosed in U.S. Pat. No. 6,552,841.

Figure 21:
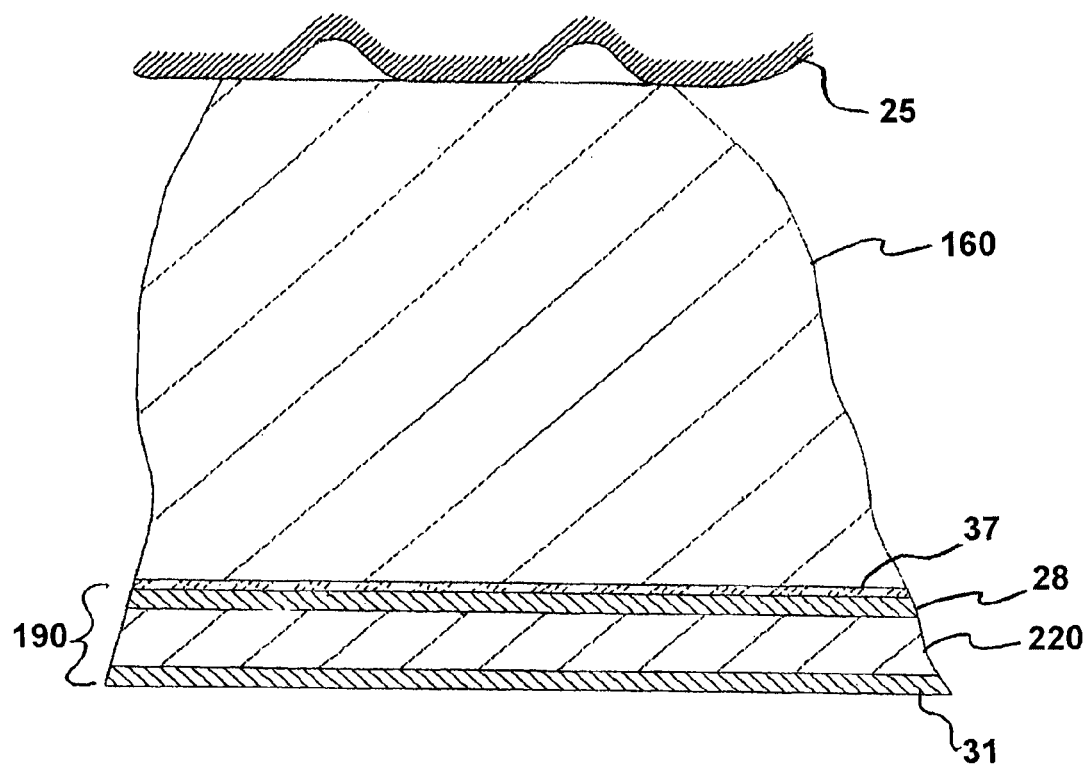
FIG. 21 is a cross-sectional view of an embodiment of a platen and generator.

FIG. 21 is a cross-sectional view of an embodiment of a platen 160 and generator 190. The generator 190 may include a piezoelectric film 220, a first metallic electrode layer 28 on a first side of the film, and a second metallic electrode layer 31 on a second side of the film 220. The metallic electrode layers 28, 31 may be sputtered or otherwise attached to the film 220. The generator 190 may be attached to the platen 160 via an adhesive 37, such as an epoxy, a two-part acrylic, or a cyanoacrylate super glue. For example, the first metallic electrode layer 28 may be attached to the platen 160 by an adhesive 37 that resides between the first electrode layer 28 and the platen 160, so as to attach the first electrode layer 28 to the platen 160. In such an embodiment, the platen 160 not only provides a surface on which a finger 25 may be placed, but also protects the generator 190, particularly from things that might damage the generator 190, like fingernails and jewelry.

Figure 22:
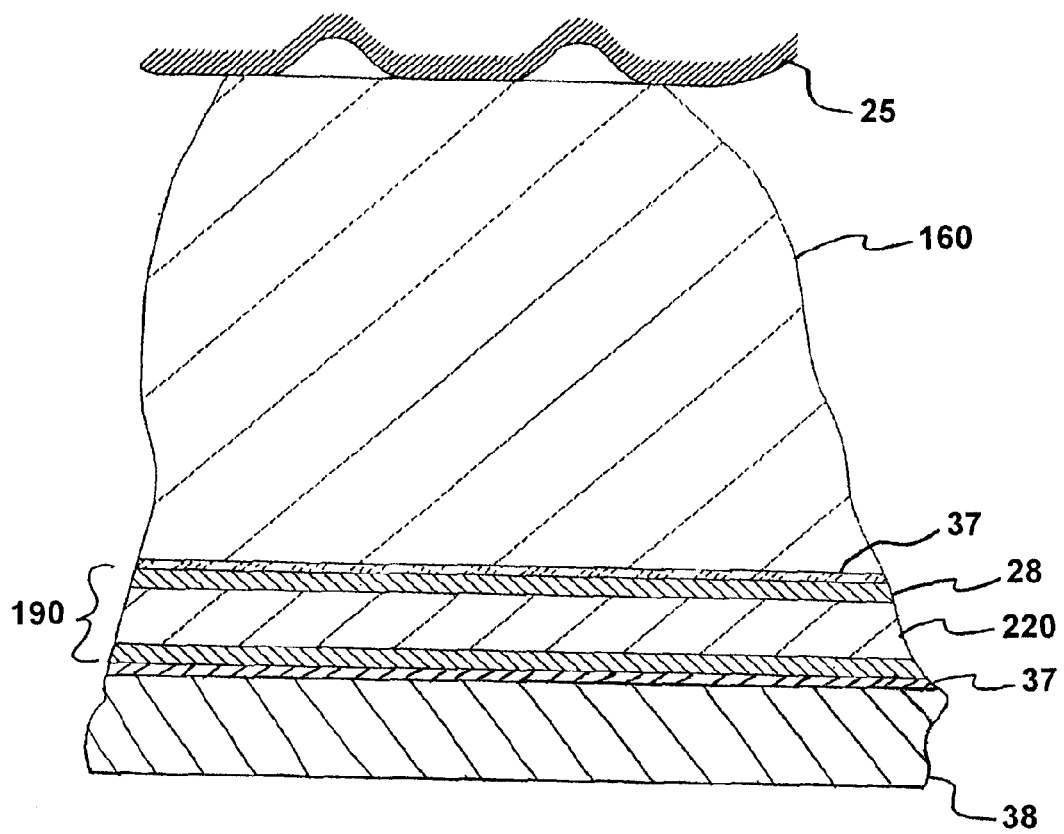
FIG. 22 depicts an embodiment similar to that shown in FIG. 21, and includes a backing plate.

FIG. 22 depicts an embodiment that is similar to that shown in FIG. 21. The embodiment of FIG. 22 includes a backing plate 38. The backing plate 38 may be fixed to the second electrode layer 31 by an adhesive 37 that resides between the second electrode layer 31 and the backing plate 38. The backing plate 38 may direct more of the ultrasonic energy from the film 220 toward the finger 25 than in the embodiment of FIG. 21. The backing plate 38 may be fixed to the platen 160, or the backing plate 38 and the platen 160 may be arranged as an integral piece, thereby embedding the generator 190. The backing plate 38 may be made from the same material as the platen 160.

Since the piezoelectric film 220 may reside substantially in a plane, the wave generated by the film 220 may be used to generate a wave that emanates in a planar fashion.

Figure 23:
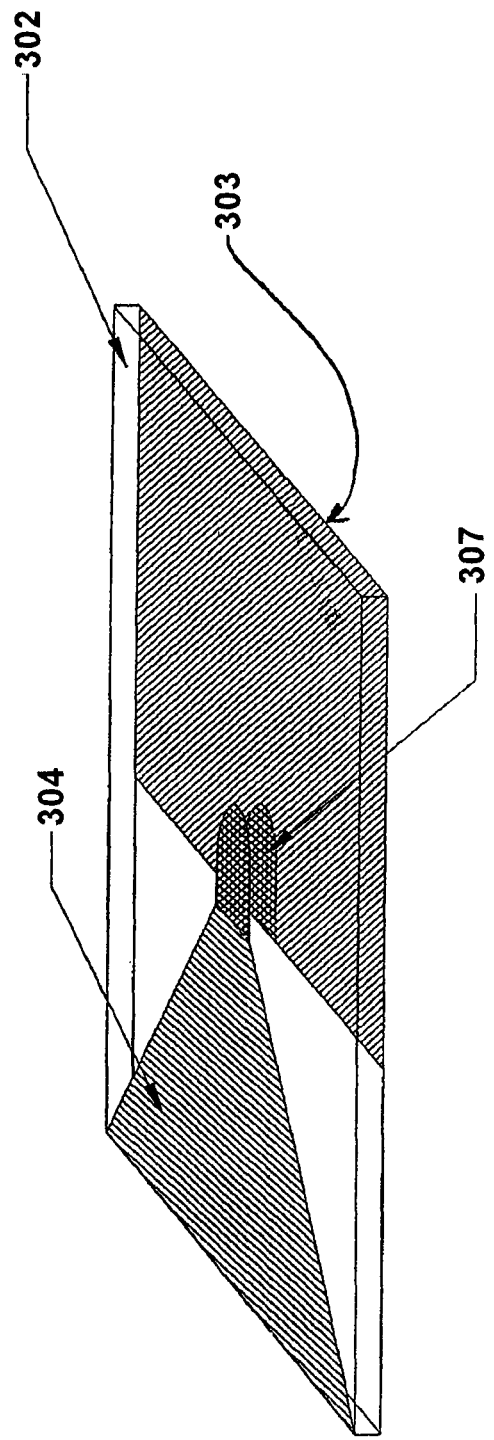
FIG. 23 is a diagram of a prior art single element acoustic film hydrophone (also called a membrane hydrophone).

FIG. 23 depicts a prior art device having a single-element hydrophone 307. This device has a small finger-like electrode 304 ("finger electrode 304") and a large area electrode 303 ("LA electrode 303"). Each of the electrodes is attached to a different side of an electret film 302 ("E film"). The molecules of the E film 302 are aligned so as to create a permanent electrostatic field. The two electrodes 303, 304 with the E film 302 between form a capacitor. When the distance between the electrodes 303, 304 changes, the voltage differential between the electrodes 303, 304 changes. The change in voltage may be detected in order to signal when pressure is being applied to the one or both of the electrodes 303, 304. In this manner, a longitudinal wave, such as an acoustic wave, may be detected.

In the prior art, a tip-portion of the finger electrode 304 is positioned relative to the LA electrode 303 such that the distance from the tip-portion of the finger electrode 304 to the LA electrode 303 is the same as the thickness of the E film 302. The E film 302 may be substantially flat and thereby defines a plane, and when viewed in a direction perpendicular to the plane, the electrodes 303, 304 may be thought of as having an overlapping area, which is shown in FIG. B1 as cross-hatched areas on each electrode 303, 304.

The overlapping area, and the E film 302 residing in that area, is commonly described as a hydrophone element 307. A first electrical connection (not shown) is made with the finger electrode 304, and a second electrical connection (not shown) is made with the LA electrode 303 in order to permit the hydrophone element 307 to detect acoustic energy impinging on the finger electrode 304 or impinging on the LA electrode 303.

Such prior art devices are often fabricated using a piece of E film 302 that is the size of a small shirt button. In such devices, the hydrophone element 307 may be a few thousandths of an inch wide. The electrodes 303, 304 are commonly formed using standard masking and sputtering techniques. In order to simplify manufacturing, the LA electrode 303 typically covers half of one side of the film 302.

The prior art devices, because of limited use and design, do not lend themselves well to mass production and are normally hand-made by skilled technicians in a very labor intensive manner.

An acoustic hydrophone array module having an outer electrode and an array of smaller inner electrodes is described. An electret film is positioned between the outer electrode and the array of inner electrodes. Each of the inner electrodes in the array may be connected directly or indirectly to a field-effect transistor ("FET"). The FETs may be arranged in an array on an insulating substrate. Information from this assembly may be used to create an image of an object that is representative of an acoustic signal emanating or reflected from the object.

The outer electrode may be formed by vacuum sputtering or may be applied as a conductive adhesive or coating film bonded directly to the electret film. Similarly the array of inner electrodes may be masked and sputtered or pre-applied to the electret film and then connected to the FET array. Alternately, each of the inner electrodes may be a conductive adhesive dot, which may be applied directly to a FET and then the array of dots may be bonded and electrically connected to the electret film.

Each of the inner electrodes may be thought of as a pixel of the acoustic image received by the outer electrode, and each of the corresponding FETs may be thought of as an amplifier of the signal received from that pixel. As the thickness of the electret element changes in response to pressure waves, the charge on the electrodes changes, and that change is detected by the FET.

The FET may be formed as a thin-film transistor ("TFT"). TFTs may be manufactured using common processes.

This document describes a limited number of embodiments of the hydrophone in order to illustrate how the hydrophone might be implemented. The embodiments described herein are meant to illustrate merely one type of hydrophone array.

Figures 24A, 24B:
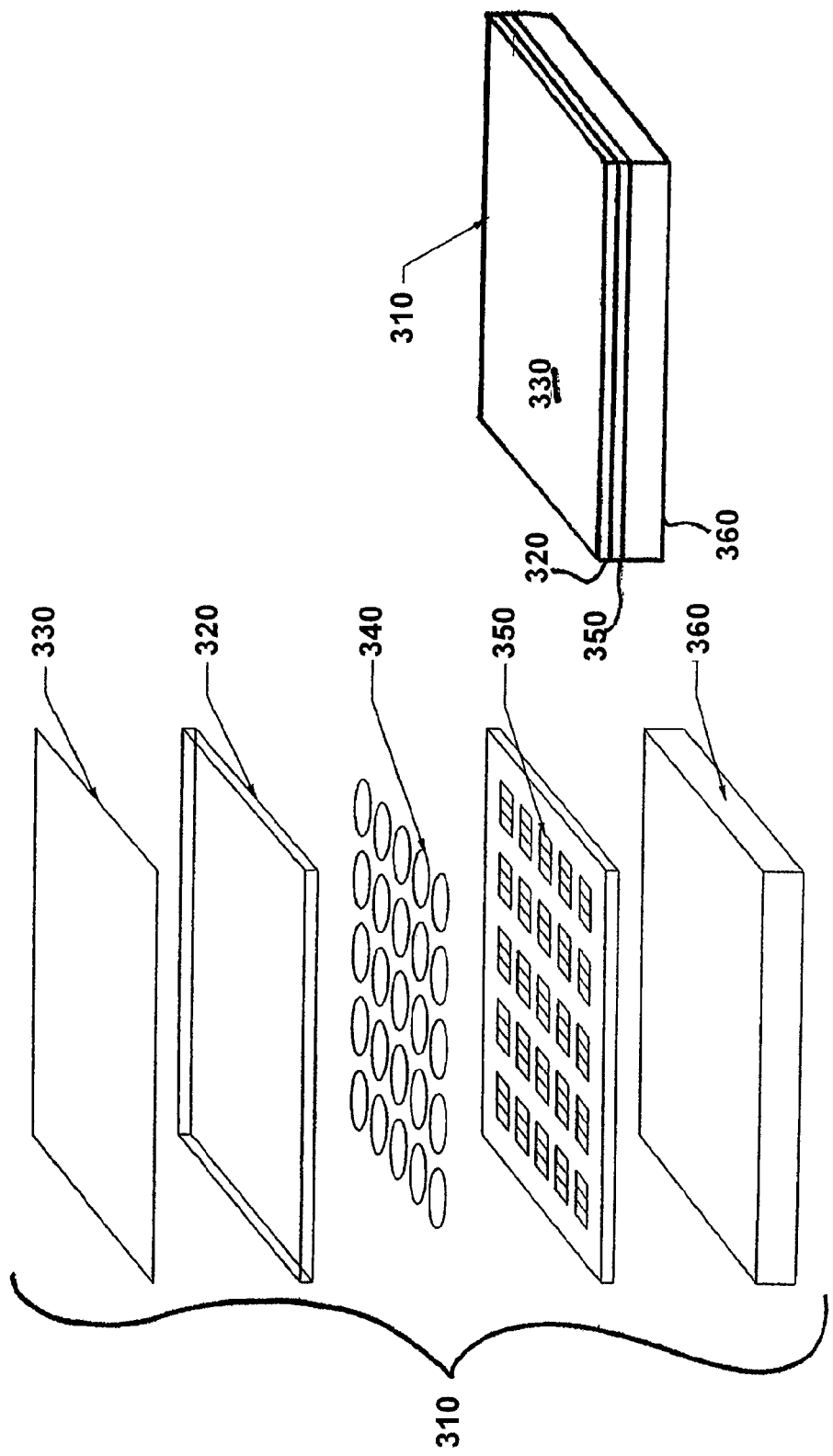
FIG. 24A is an exploded perspective view of an embodiment of the hydrophone.
FIG. 24B shows the device of FIG. 24A in assembled form.

FIG. 24A is an exploded perspective view showing certain components of a hydrophone array 310. FIG. 24B shows the hydrophone array 310 in assembled form. An outer electrode 330 has been applied to one side of an electret film 320 and an array of inner conductive electrodes 340 have been applied to the other side of the electret film 320. Applying the electrodes 330, 340 may be accomplished by various means that may include masked and sputtered deposition or adhesive bonding. The outer electrode 330 and/or inner conductive electrodes 340 may also be created by masking and etching. The resulting assembly may then be aligned and bonded to an array 350 of TFTs (thin film transistors). Each TFT may be a field-effect transistor ("FET") or group of FETs (or similar electrical components) that have been formed on an insulating substrate 360. Alternately, an adhesive layer, having the inner conductive electrodes 340 thereon, may be deposited to the TFT/FET array, and the film 320 may then be aligned, laid down and bonded to the TFT array directly. Each TFT may function as a switch corresponding to a portion of outer electrode 330. For example, the gate of each TFT may be electrically connected to one of the inner conductive electrodes 340. Each portion of the outer electrode 330 may be thought of as a pixel. The voltage across each pixel may be controlled independently and at a high contrast ratio.

TFT manufacturing for flat panel applications is a standard process, which should reduce the cost of the hydrophone array 310. TFTs may be fabricated by depositing and patterning metals, insulators, and semiconductors on substrates through methods well known in the art. TFTs typically employ amorphous silicon, CdSe film, or semiconducting polymers as the semiconductor material. Amorphous silicon is typically used in flat panel applications as it is easily deposited on large area glass or plastic substrates. Since a TFT is economical to manufacture and has already been successfully incorporated into flat panel applications, use of this technology should result in the production of an acoustic hydrophone array at low cost.

Figure 25:
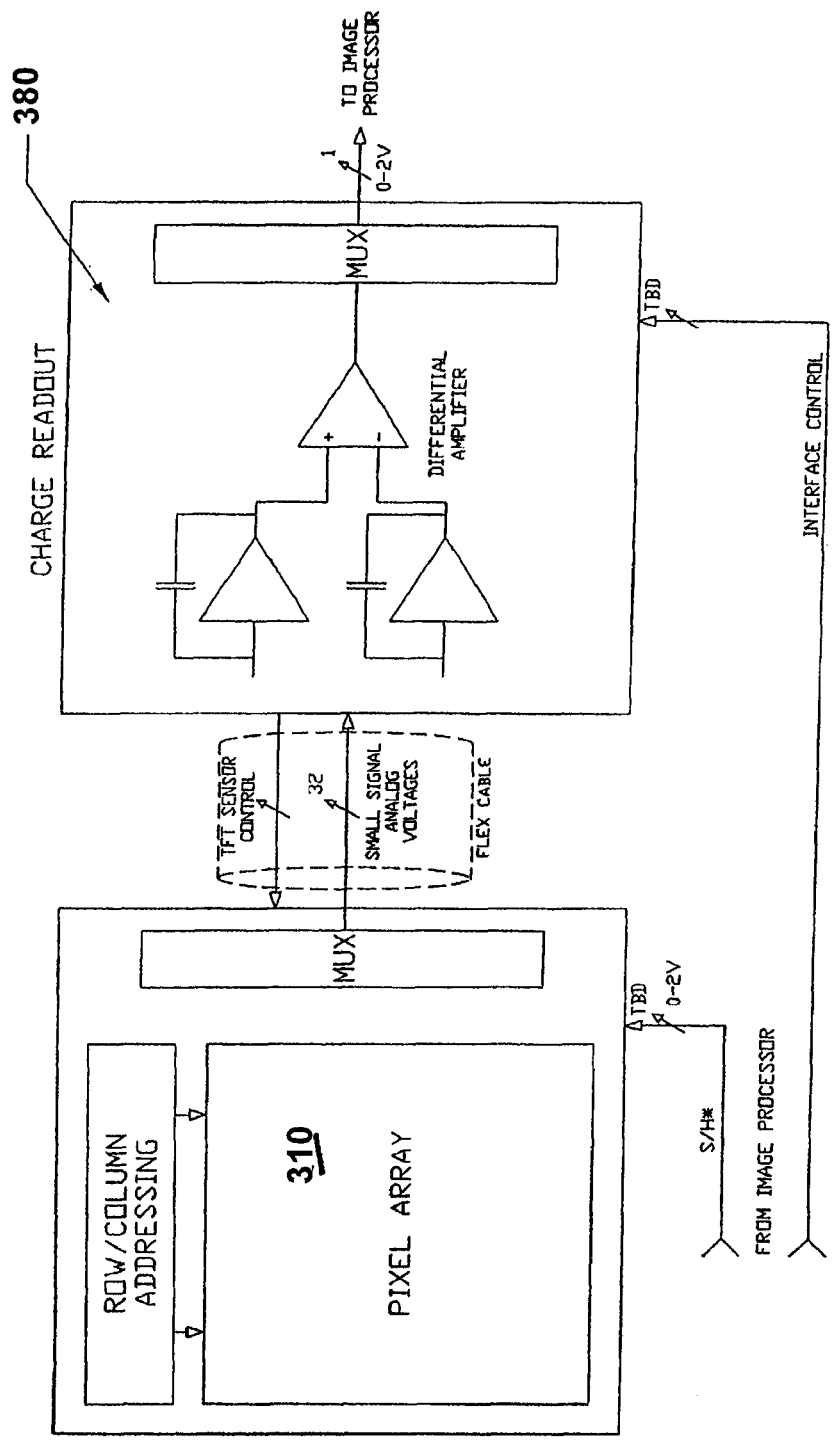
FIG. 25 is a schematic diagram of a typical TFT sensor and charge readout system suitable for application as a hydrophone array device.

With reference to FIG. 25, the hydrophone array 310 may make use of the various strengths of typical TFT array technology (row and column addressing, multiplexer components and sample and hold circuitry). The hydrophone array 310 may be electrically connected to a charge readout device 380, which may be used to address and amplify the low level signals available from each of the FETs into higher level signals that can then be subsequently passed to an A/D converter and image processing circuitry in order to produce a grayscale image suitable for subsequent applications, such as medical imaging or biometric identification.

Figure 26:
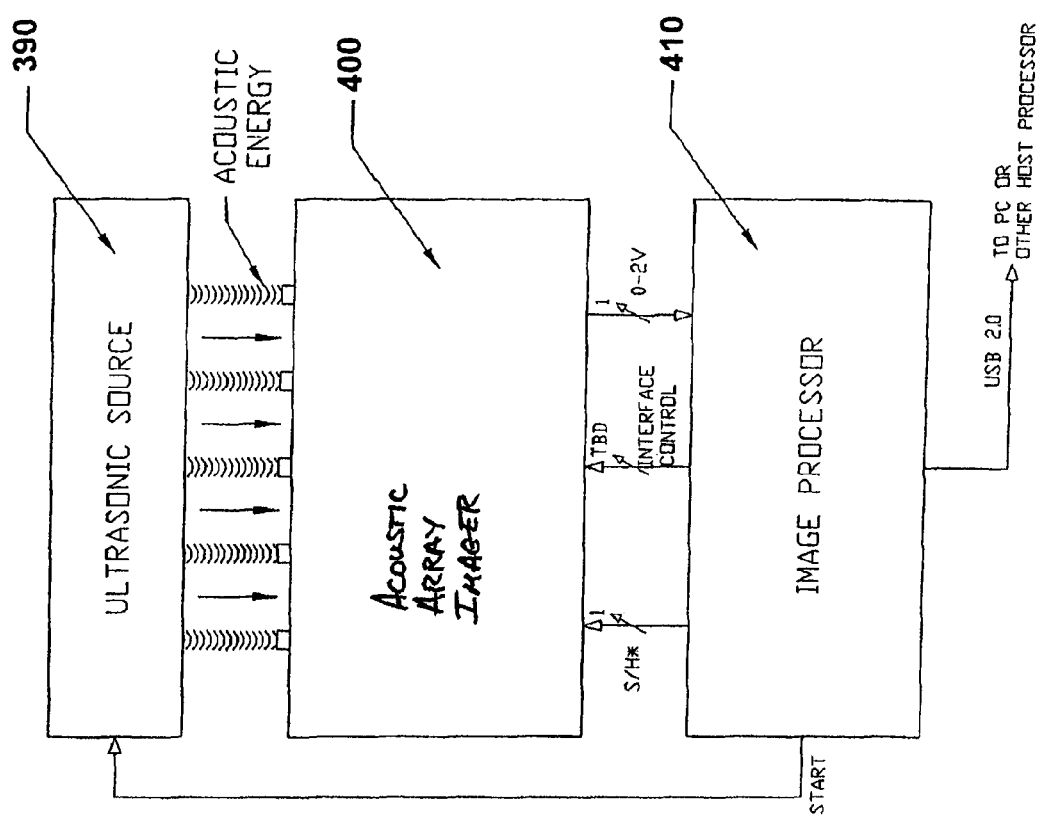
FIG. 26 is a block diagram of an embodiment of an acoustic hydrophone array device.

FIG. 26 depicts a system in which an ultrasonic image source 390 sends acoustic energy to an acoustic array imager 400, such as the hydrophone array 310. The acoustic array imager 400 provides signal information to an image processor 410 that performs post processing on the collected information in order to generate an image of the ultrasonic source 390.

It should be recognized that a commercially useful version of the hydrophone array 310 shown in FIG. 24 may have many more sensor elements than are shown in FIG. 24. In such a device, each of the inner conductive electrodes 340 may be addressable, and therefore may be thought of as an addressable pixel.

The hydrophone array may use TFT panels that are available in configurations suitable as an output device or an input device (a sensor). The topology of TFT panels may differ in component specifics, and yet such differing panels may still offer equivalent performance. This document does not attempt to describe in detail the manufacturing process of a TFT array, but rather recognizes that TFT arrays are available.

The voltage output of the capacitor having the electret film 320 and the voltage required to operate the TFT array may be different, and so certain components may need to be employed in order for the TFT array and the film 320 to be compatible. For example, a buffer, an amplification stage, rectification or attenuation may be needed in order to provide an appropriate voltage input to the FET of a specific TFT sensor panel.

The electret detector elements and TFTs can provide an effective and economical alternative to conventional hydrophone devices. Electret detectors and TFTs may be manufactured with corresponding readout TFTs using conventional methods thereby reducing mask counts and costs. Electret detectors and TFTs may yield electric currents greater than that of conventional hydrophones.

A hydrophone array such as is taught in this document may be useful in medical or dental imaging applications, such as non x-ray mammograms or soft and hard tissue examination.

Those skilled in the art will recognize that this invention is not limited to the embodiments and applications disclosed. They will also recognize that for any configuration presented that the mechanics of imaging a same size image, an enlarged image or a reduced image may be similar in practice and that they may differ in the optics system selected for the particular embodiment.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A biometrical object reader, comprising:
a first acoustic waveguide array;
a second acoustic waveguide array;
a plane wave generator positioned between the first acoustic waveguide array and the second acoustic waveguide array, wherein the plane wave generator includes a piezoelectric film and a pair of electrodes that are in contact with opposite surfaces of the piezoelectric film;
and wherein the acoustic waveguide arrays are positioned to receive ultrasonic energy from the plane wave generator and guide the received ultrasonic energy away from the plane wave generator,
an ultrasonic detector array positioned to receive via one of the waveguide arrays ultrasonic energy reflected from a biological object being imaged; and
an image generator that creates an image of the object using the ultrasonic energy received by the detector array.

* * * * *